(12) United States Patent
Park et al.

(10) Patent No.: US 6,464,645 B1
(45) Date of Patent: *Oct. 15, 2002

(54) ULTRASONIC TRANSDUCER ASSEMBLY CONTROLLER

(75) Inventors: William J. Park, San Jose; Douglas B. Dull, Palo Alto, both of CA (US); John W. Eaton, TOURS Cedex 1 (FR); Robert A Howard, Palo Alto; Stephen L. Ijams, Los Alto, both of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/434,594

(22) Filed: Nov. 5, 1999

Related U.S. Application Data (63) Continuation-in-part of application No. 09/215,970, filed on Dec. 18, 1998, now abandoned, which is a continuation-in-part of application No. 08/792,897, filed on Jan. 31, 1997, now Pat. No. 5,954,654.

(51) Int. Cl.$^7$ ................................................ A61B 8/12
(52) U.S. Cl. ..................................................... 600/462
(58) Field of Search ................................. 600/459–463, 600/446, 439, 607, 122, 604, 95, 264, 280, 282

(56) References Cited

U.S. PATENT DOCUMENTS

| | | |
|---|---|---|
| 4,207,873 A | 6/1980 | Kruy |
| 4,435,614 A | 3/1984 | McAusland |
| 4,474,174 A | 10/1984 | Petruzzi |
| 4,605,009 A | 8/1986 | Pourcelot et al. |
| 4,794,931 A | 1/1989 | Yock |
| 4,841,976 A | 6/1989 | Packard et al. |
| 4,951,677 A | 8/1990 | Crowley et al. |
| 5,190,050 A | 3/1993 | Nitzsche |
| 5,207,225 A | 5/1993 | Oaks et al. |
| 5,275,151 A | 1/1994 | Shockey et al. |
| D347,473 S | 5/1994 | Nitzsche |

(List continued on next page.)

OTHER PUBLICATIONS

"Ultrasonic Transducer Assembly Controller," U.S. Patent Application Serial No. 29/113,501, filed Nov. 5, 1999; inventors: Richard W. Henderson, Jeff Gamelsky, Glenn Hansen, Gill Wong, and William J. Park.

"Medical Diagnostic Ultrasound Catheter with Dielectric Isolation," U.S. Patent Application Serial No. 09/401,632, filed Sep. 22, 1999; inventors: Randall L. Schlesinger and Mathew Rahimi.

*Primary Examiner*—Francis J. Jaworski (57) ABSTRACT

A controller for an ultrasonic transducer assembly includes a housing having a longitudinal axis that extends generally parallel to the proximal end of a conduit, such as a catheter. A steering actuator is mounted to the housing for rotation about the longitudinal axis, and a steering hub is mounted for rotation in the housing and coupled to the steering actuator such that rotation of the steering ring with respect to the housing causes rotation of the steering hub. A steering line is secured adjacent the steering hub and extends to the distal end of the conduit such that rotation of the steering hub alters the effective length of the steering line to steer the distal end. The steering line is wrapped at least partially around a stator to avoid threading the steering line through multiple holes and slots prior to termination to the steering hub. The steering line is preferably formed of a liquid crystal polymer, and the housing of the steering mechanism preferably contains an extension portion to ensure that the portion of the housing that the user grips to manipulate the steering mechanism is sufficiently far away from the cable to ensure that the cable will remain sterile and thus reusable. In an additional preferred embodiment, the controller is contoured to a human hand to provide a comfortable, efficient, and enjoyable one-handed operation.

20 Claims, 9 Drawing Sheets

U.S. PATENT DOCUMENTS

| | | |
|---|---|---|
| 5,322,064 A | 6/1994 | Lundquist |
| 5,336,182 A | 8/1994 | Lundquist et al. |
| 5,345,940 A | 9/1994 | Seward et al. |
| 5,351,692 A | 10/1994 | Dow et al. |
| 5,359,994 A | 11/1994 | Krauter et al. |
| 5,364,352 A | 11/1994 | Cimino et al. |
| 5,368,037 A | 11/1994 | Eberle et al. |
| 5,383,852 A | 1/1995 | Stevens-Wright |
| 5,383,923 A | 1/1995 | Webster, Jr. |
| 5,385,148 A | 1/1995 | Lesh et al. |
| 5,395,327 A | 3/1995 | Lundquist et al. |
| 5,395,329 A | 3/1995 | Fleischhackor et al. |
| 5,397,304 A | 3/1995 | Truckai |
| 5,398,689 A | 3/1995 | Connor et al. |
| 5,402,793 A | 4/1995 | Gruner et al. |
| 5,413,107 A | 5/1995 | Oakley et al. |
| 5,431,168 A | 7/1995 | Webster, Jr. |
| 5,439,006 A | 8/1995 | Brennen et al. |
| 5,453,575 A | 9/1995 | O'Donnell et al. |
| 5,456,258 A | 10/1995 | Kondo et al. |
| 5,462,527 A | 10/1995 | Stevens-Wright et al. |
| 5,465,716 A * | 11/1995 | Avitall .......... 606/41 |
| 5,479,930 A | 1/1996 | Gruner et al. |
| 5,489,270 A | 2/1996 | Van Erp |
| 5,492,126 A | 2/1996 | Hennige et al. |
| 5,512,035 A | 4/1996 | Konstorum et al. |
| 5,514,115 A | 5/1996 | Frantzen et al. |
| 5,527,279 A | 6/1996 | Imran |
| 5,531,685 A | 7/1996 | Hemmer et al. |
| 5,545,200 A * | 8/1996 | West et al. .......... 607/122 |
| 5,571,085 A | 11/1996 | Accisano, III |
| D381,076 S | 7/1997 | Thornton et al. |
| 5,656,030 A * | 8/1997 | Hunjan et al. .......... 604/95 |
| 5,662,119 A * | 9/1997 | Brennan et al. .......... 600/585 |
| 5,662,606 A | 9/1997 | Cimino et al. |
| D384,743 S | 10/1997 | Chia |
| 5,722,402 A | 3/1998 | Swanson et al. |
| 5,722,403 A | 3/1998 | McGee et al. |
| 5,741,320 A * | 4/1998 | Thornton et al. .......... 607/122 |
| 5,876,345 A | 3/1999 | Eaton et al. |
| 5,938,616 A | 8/1999 | Eaton et al. |
| 5,954,654 A | 9/1999 | Eaton et al. |

* cited by examiner

ULTRASONIC TRANSDUCER ASSEMBLY CONTROLLER

RELATED APPLICATIONS

This is a continuation-in-part of application Ser. No. 09/215,970, filed Dec. 18, 1998, now abandoned which is a continuation-in-part of application Ser. No. 08/792,897, filed Jan. 31, 1997 (now U.S. Pat. No. 5,954,654), both of which are hereby incorporated by reference.

BACKGROUND

Catheter-mounted ultrasonic transducers are known to the art, as described for example in U.S. Pat. No. 4,794,931 and 5,368,037. These catheter-mounted transducers are single use, disposable devices which provide a radial image format either by means of a radial phased array or a rotating crystal. These devices do not include any mechanism for steering or articulating the tip of the catheter. Because the catheter tip cannot be steered, it is in general not possible to position the transducer optimally to obtain different views of the tissue or structure being imaged.

Catheters other than ultrasonic imaging catheters currently exist which have articulating tips. One typical steering mechanism for such a catheter uses a knob which rotates about an axis perpendicular to the length of the catheter. As the user rotates the knob clockwise or counterclockwise, the tip of the catheter will articulate either up and down, or left and right. In addition to manipulating the catheter tip with the knob, the catheter is generally rotated within the vessel by rotating the control housing. Such rotation of the control housing causes the knob to rotate as well as the catheter, and can place the knob in an relatively inaccessible position for the user. Awkward positioning of the steering knob can make manipulating the catheter tip difficult.

Accisano U.S. Pat. No. 5,571,085 and Fleischhackor U.S. Pat. No. 5,395,329 disclose control handles for steerable catheters which utilize a rotating collar to move a slide longitudinally in the catheter handle. Steering lines are connected to the slide such that reciprocation of the slide steers the distal tip of the catheter. This arrangement provides the advantage of a steering actuator which extends around the complete circumference of the handle and rotates about the longitudinal axis of the handle.

SUMMARY

The present invention is defined by the following claims, and nothing in this section should be taken as a limitation on those claims. By way of introduction, the preferred embodiments described below relate to controlling an ultrasonic transducer assembly.

In one preferred embodiment, a steering mechanism is provided for an ultrasonic transducer assembly of the type comprising an elongated conduit comprising a distal end portion and a proximal end portion, a plurality of ultrasonic transducer elements carried by the conduit adjacent the distal end portion, and at least one steering line carried by the conduit.

The steering mechanism comprises a housing defining a longitudinal axis extending generally parallel to the proximal portion of the conduit, an actuator such as a steering ring is carried by the housing for rotation about the longitudinal axis, and a steering hub mounted for rotation in the housing and coupled to the actuator such that rotation of the actuator with respect to the housing about the longitudinal axis causes rotation of the steering hub.

The steering line is secured adjacent the steering hub such that rotation of the steering hub alters the effective length of the steering line to steer the distal end of the conduit. Unlike other steering mechanisms in which the steering line is threaded through multiple holes and slots prior to termination to the steering hub, in the steering mechanism of this preferred embodiment, the steering line wraps at least partially around the diameter of a stator. This not only makes the steering mechanism easier to assemble, but it also reduces the amount of friction on the steering line.

In another preferred embodiment, a steerable, catheter-mounted ultrasonic transducer assembly is provided comprising an elongated conduit and a plurality of transducer elements as described above. A steering mechanism is coupled to the proximal portion of the conduit, and at least one steering line interconnects the steering mechanism and the distal end portion of the conduit. In one preferred embodiment, the steering line comprises a braided yarn spun from a liquid crystal polymer. In another preferred embodiment, the steering line comprises a liquid-crystal-polymer-extruded monofilament. Such steering lines can withstand high catheter processing temperatures and can withstand being under a load for an extended period of time without stretching.

In yet another preferred embodiment, the steering mechanism is part of a housing that removablely connects to a cable of a medical diagnostic ultrasonic imaging system. In this preferred embodiment, the housing comprise an extension portion to ensure that the portion of the housing that the user grips to manipulate the steering mechanism is sufficiently far away from the cable to ensure that the cable will remain sterile and thus reusable.

In an additional preferred embodiment, a controller for an ultrasonic transducer assembly is provided that is contoured to a human hand to provide a comfortable, efficient, and enjoyable one-handed operation of controls on the controller.

Though these preferred embodiments are preferably used together as described below, they can, if desired, be used independently of one another. For example, the preferred steering mechanism can be used with conventional, metal steering lines, and conversely the preferred steering lines can be used with conventional steering mechanisms with or without a housing with an extension portion.

The preferred embodiments will now be described in reference to the attached drawings.

DETAILED DESCRIPTION OF THE PRESENTLY PREFERRED EMBODIMENTS

Figure 1:
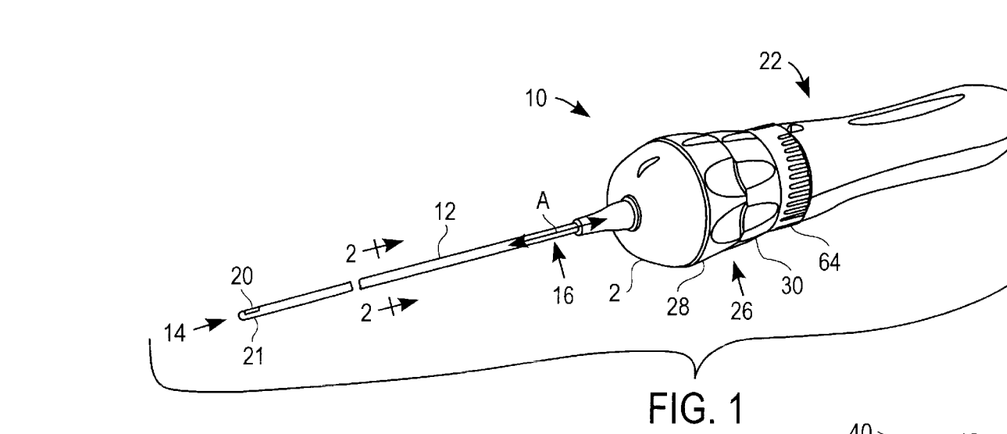
FIG. 1 is a perspective view of an ultrasonic transducer assembly of a presently preferred embodiment.

Turning now to the drawings, FIG. 1 shows a perspective view of a transducer assembly 10 that incorporates a preferred embodiment of this invention. The transducer assembly 10 includes an elongated catheter 12 having a distal end 14 and a proximal end 16. A linear array of transducer elements 20 is carried by the distal end 14 of the catheter 12. The transducer elements 20 can be arranged in a linear or a curvilinear phased array, depending upon the application. The portion of the catheter 12 immediately proximal to the transducer elements 20 is formed of a lower hardness polymer enabling it to articulate or steer in any of four directions (up/down and left/right).

The catheter 12 is mounted in a housing 22 that connects to a cable of a medical diagnostic ultrasonic imaging system (not shown). The housing 22 includes a nose cap 2 and also includes a steering mechanism 26 that in turn includes first and second actuators, which in this embodiment take the form of steering rings 28,30. The first steering ring 28, when rotated, causes the distal end 14 to move in a first plane, and the second steering ring 30, when rotated, causes the distal end 14 to articulate in a second plane, transverse to the first plane. For example, the first steering ring 28 can cause the distal end 14 to move in the anterior/posterior plane, and the second steering ring 30 can cause the distal end 14 to move in the left/right plane. As shown in FIG. 1, the first and second steering rings 28,30 extend circumferentially around the housing 22 and each pivots about an axis A, which is parallel to the centerline of the catheter 12 adjacent the proximal end 16. The steering mechanism 26 also includes a brake knob 64 that is rotatable about axis A.

Figure 2:
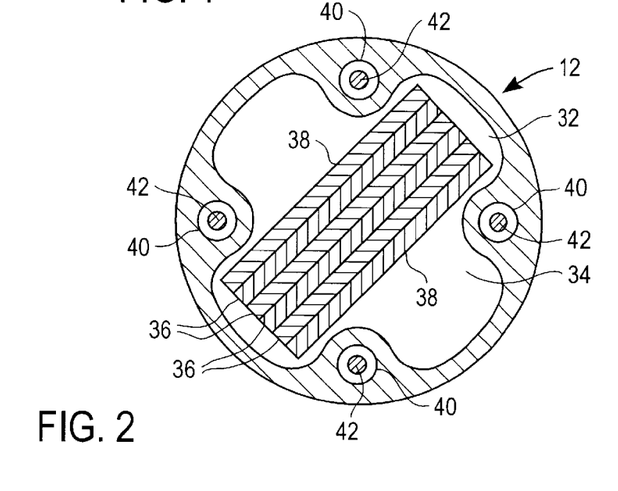
FIG. 2 is a cross-sectional view taken along line 2—2 of FIG. 1.

Turning now to FIG. 2, the catheter 12 includes a conduit 32 that defines a central lumen 34. The central lumen 34 carries a stack of flexible circuit strips 36, 38. The flexible circuit strips 36 transmit signals to the transducer elements and receive signals from the transducer elements. The flexible circuit strips also include ground return paths. The flexible circuit strips 38 are provided with uninterrupted copper shields extending over their entire width and length in order to reduce EMI interference to and from the catheter 12. These shields are preferably not connected to the transducer elements.

The conduit 32 also defines four smaller lumens 40, and each of the lumens 40 carries a respective steering line 42. In this embodiment, the steering lines 42 are formed in diametrically opposed pairs, and the steering lines 42 within each pair are continuous from the steering mechanism 26 to the proximal portion of the transducer elements 20 (FIG. 1). The steering line makes a reverse curve at this point and is secured in place to the distal end of a short segment 21 of conduit (approximately 1.5 inches in length) that is integral with the main conduit and is of substantially lower hardness than the body of the catheter. As described below, by increasing tension on one steering line while relieving tension on the diametrically opposed steering line, this lower hardness portion will be preferentially compressed and can bend or be steered in either of two transverse planes. As used herein, the term "set of steering lines" means one or more steering lines.

Figure 3:
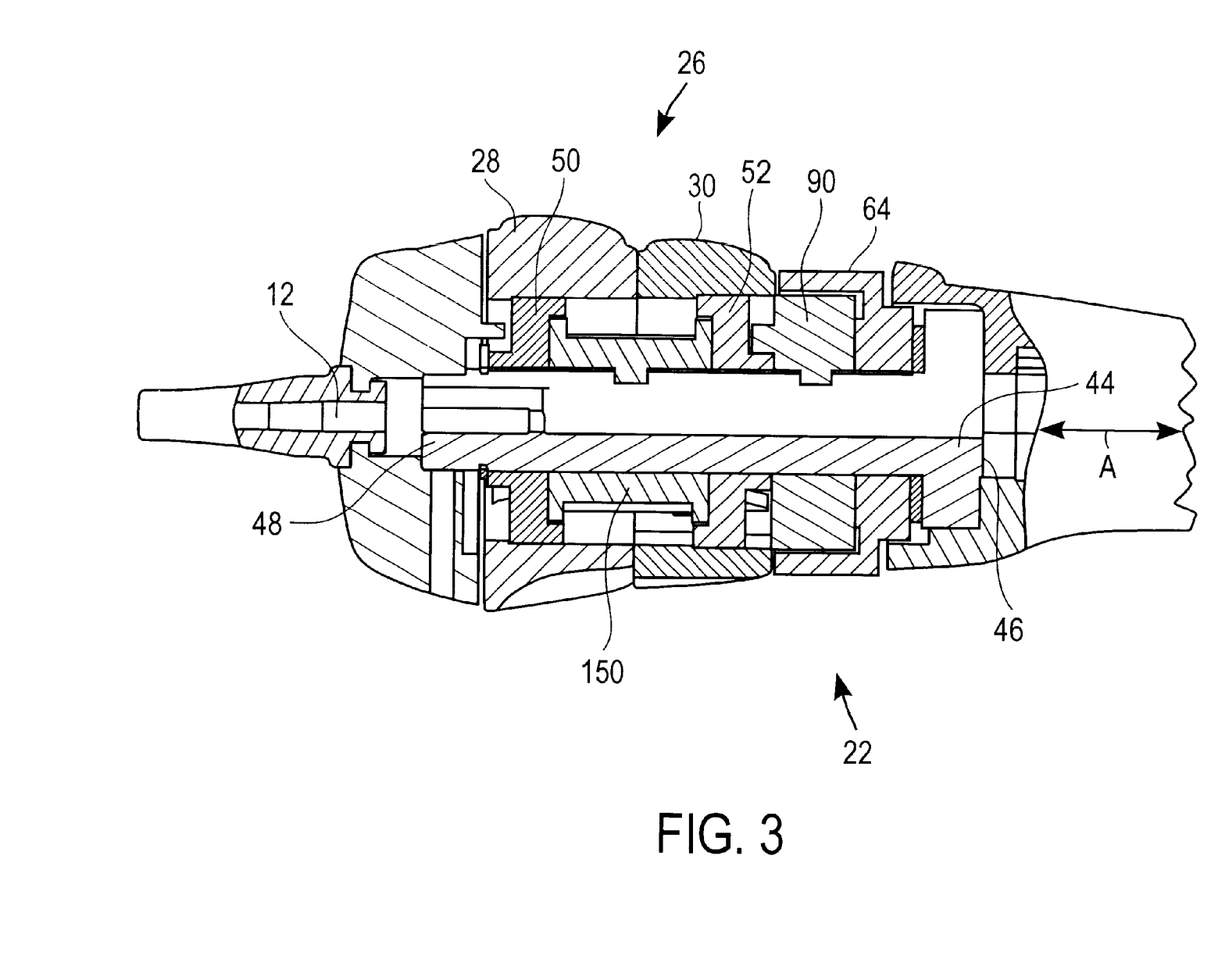
FIG. 3 is a cross-sectional view of a portion of the handle of the embodiment of FIG. 1.

FIG. 3 shows a cross-sectional view of the steering mechanism 26. The steering lines 42 have been deleted for clarity. As shown in FIG. 3, the steering mechanism 26 includes a central shaft 44 that is fixed in place to the proximal portion 46 of the housing 22. This shaft 44 supports at its forward end 48 the catheter 12. The shaft 44 also supports the first and second steering hubs 50, 52 for rotation about axis A. The steering hubs 50,52 support the first and second steering rings 28,30. In this embodiment, the steering hubs 50, 52 are integrally formed with the steering rings 28, 30, respectively, and rotate with them as a unit. Each of the first and second steering rings 28,30 define an annular shape that is accessible around the complete circumference of the housing 22.

Also as shown in FIG. 3, the shaft 44 fixedly supports a stator 150 between the first and second steering hubs 50, 52. Other elements of the steering mechanism 26 shown in FIG. 3 include a brake knob 64 which is mounted for rotation on the shaft 44 and is coupled with a brake rotor 90. Rotation of the brake knob 64 causes the brake rotor 90 to compresses against the first and second steering hubs 50, 52 and the stator 150, thereby immobilizing both steering rings 28, 30. When the brake knob 64 is rotated in the opposite direction, pressure is removed from the first and second steering hubs 50, 52 and the stator 150, and the steering rings 28,30 can be rotated independently of one another to steer the catheter 12 as desired.

Figure 4:
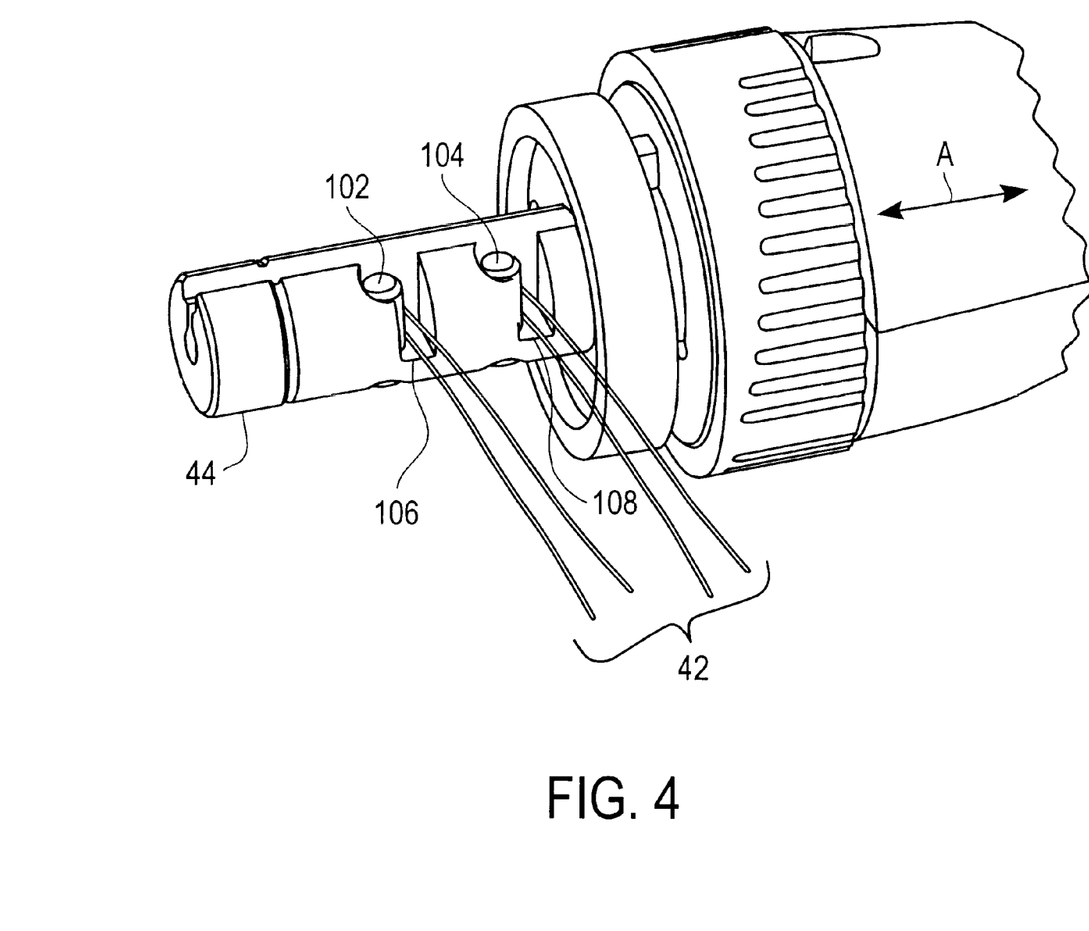
FIGS. 4–6 are exploded, perspective views of a preferred ultrasonic transducer assembly.
Figure 5:
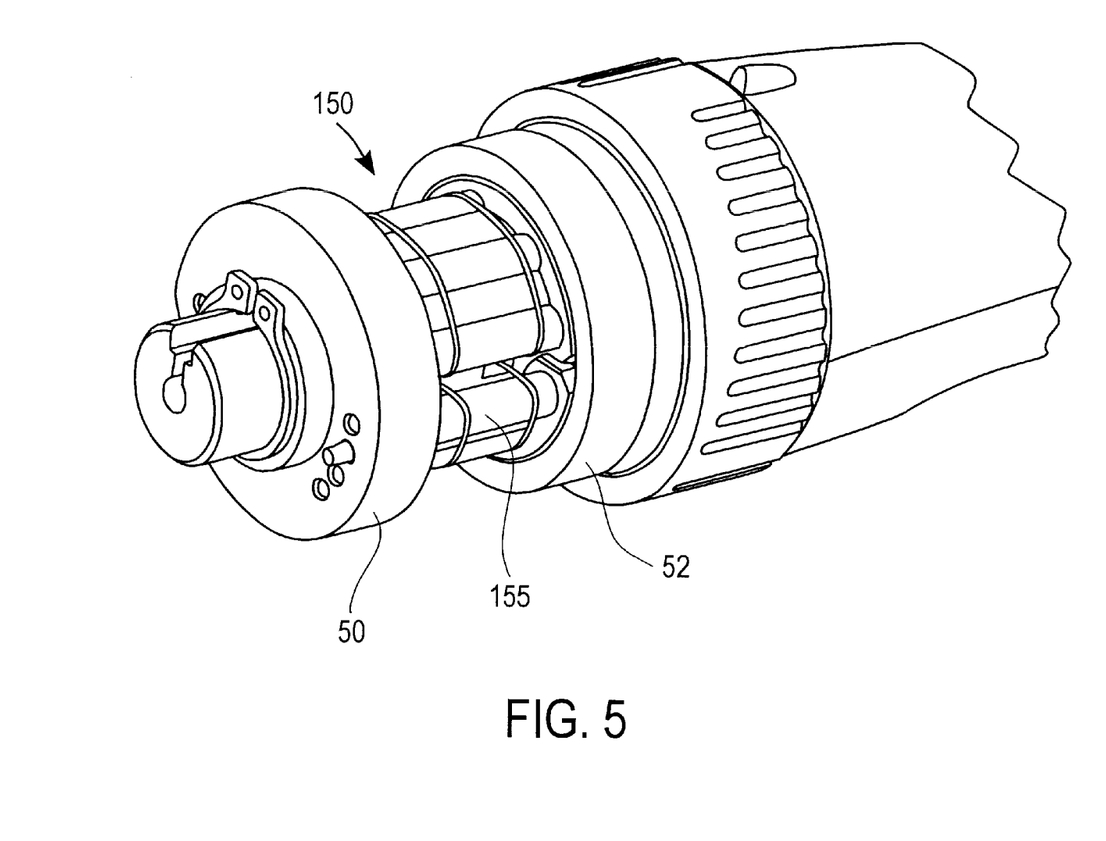
Figure 6:
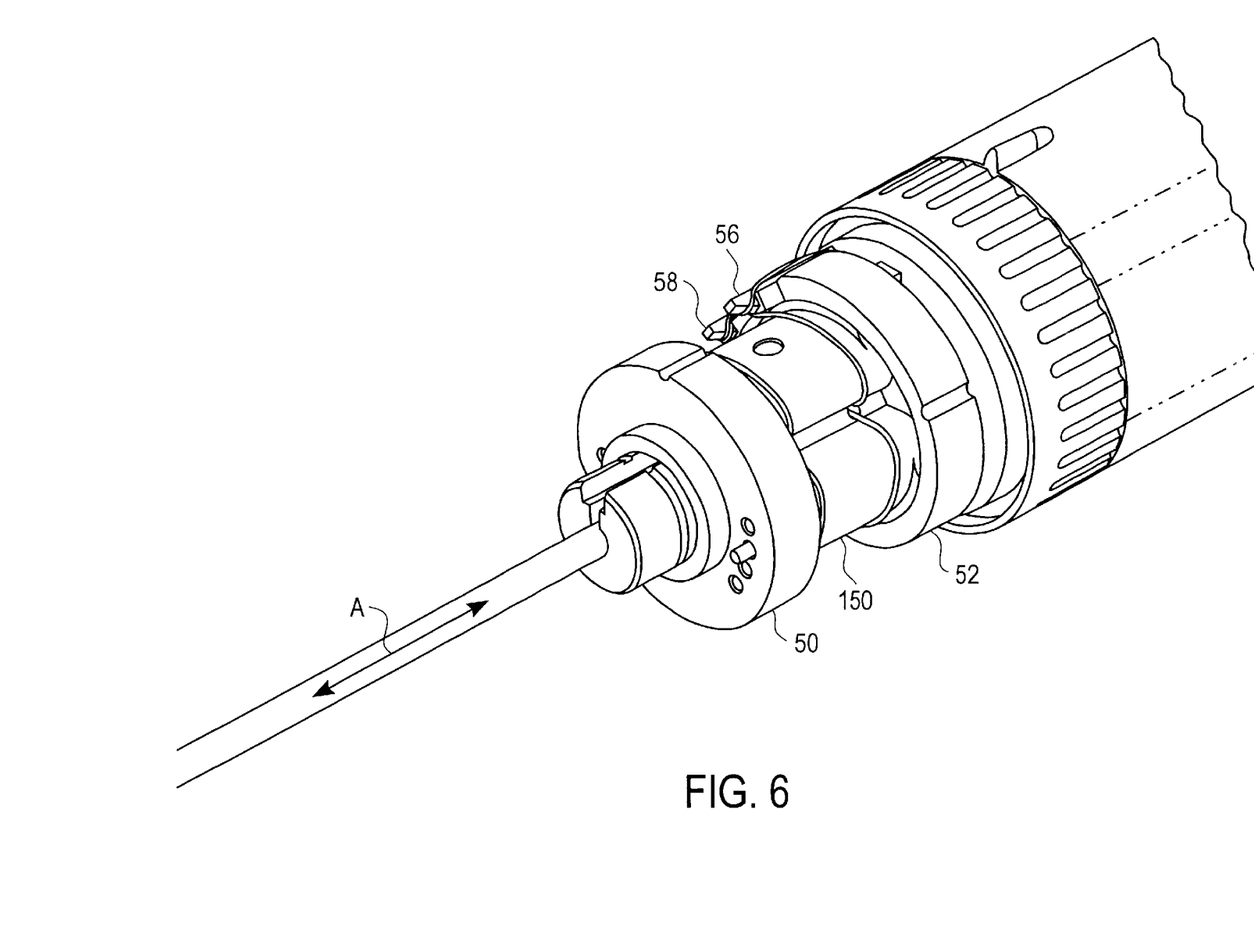

FIGS. 4–6 illustrate the positioning and the operation of the steering lines 42. FIG. 4 is a partially exploded perspective view showing the manner in which the steering lines 42 from the catheter 12 are passed from the shaft 44. The shaft 44 defines a first and second slot 106, 108 adapted to route the steering lines 42 therethrough from longitudinal axis A. Diametrically opposed pairs of steering lines 42 pass from the first and second slots 106, 108. In this preferred embodiment, bearings 102, 104 are located adjacent to the first and second slots 106, 108, respectively. These bearings, which are preferably highly-polished metal pins or rollers, reduce the amount of friction on the steering lines 42 as they exit the shaft 44.

As shown in FIG. 5, the steering lines 42 are wrapped at least partially around the outer diameter of the stator 150. In this preferred embodiment, the stator 150 comprises a set of bearings 155 positioned around its outer diameter. As used herein, the term "set of bearings" means one or more bearings. Like the bearings adjacent to the slots 106, 108 in the shaft 44, this set of bearings 155 preferably includes highly-polished metal pins or rollers, which reduce the amount of friction on the steering lines 42 as they pass around the outer diameter of the stator 150. In addition to increasing the life of the steering lines 42, the set of bearings 155 reduces the force required for articulation, thereby providing smooth-feeling articulation. Of course, the outer diameter of the stator 150 need not have a set of bearings, as shown in FIG. 6. Diametrically opposed steering lines 44 are secured to the first and second steering hubs 50, 52. In the preferred embodiment shown in FIG. 6, the steering lines 44 secure to two termination points 56, 58 on the second steering hub 52 and two termination points (not shown) on the first steering hub 50.

In operation, the steering hubs 50, 52 are carried by the steering rings 28, 30 for rotation about longitudinal axis A, such that rotation of a steering ring, and hence of a steering hub, alters the effective length of a steering line to steer the distal end. When the steering rings 28, 30 are placed in a neutral position, the distal end 14 of the catheter 12 is not deflected. When a respective steering ring 28,30 is rotated, one of the corresponding pair of steering lines 42 is increased in effective length, and the other is decreased in effective length. This causes the distal end 14 of the catheter 12 to be steered in the respective plane. Because the steering rings 28,30 extend in an uninterrupted fashion around the circumference of the housing 22, the steering rings 28,30 are always accessible to the user, regardless of the rotational position of the housing 22. Because the steering hubs 50,52 rotate around the same axis as the steering rings 28,30, the steering mechanism is relatively simple in construction and operates substantially without play.

There are several advantages associated with these preferred embodiments. First, unlike other steering mechanisms, the steering lines 42 are not threaded through multiple holes and slots prior to termination to the steering hubs 50, 52, thereby making the steering mechanism much easier to assemble. Second, because the stator 150 is positioned between the steering hubs 50, 52, the steering lines 42 can terminate on one steering hub without passing through the other steering hubs. In this way, the position of one of the steering hubs does not affect the amount of actuation of the other steering hub. Lastly, because of the relatively large bend radius of the stator 150, the steering lines 42 are subject to less friction, thereby increasing the durability of the steering lines 42.

It is preferred that the steering lines 42 be formed of a braided yarn spun from a liquid crystal polymer. Preferably, the liquid crystal polymer is the one sold under the tradename Vectran®, which can be purchased from Hoechst-Celanese Corporation. It is preferred that the Vectran® braid be approximately 0.010 inches in diameter with a pull strength of approximately 20 pounds. A suitable braider is Woodstock Line Company. It has been found that this preferred steering line can better withstand the high catheter processing temperatures than stranded polymers, such as the one sold under the tradename Spectra®. Additionally, unlike Spectra®, Vectran® has very low creep characteristics, allowing it to better withstand stretching while under load for an extended period of time. In addition to a braided yarn, the liquid crystal polymer can be extruded into a monofilament.

In addition, the catheter may be formed as described in U.S. Pat. No. 5,846,205, and the flexible circuits of the catheter may be fabricated as described in U.S. Pat. No. 5,795,299, both assigned to the assignee of the present invention. The entire disclosures of both of these patents are hereby incorporated by reference.

There are several alternatives to the preferred embodiments described above. For example, the preferred steering lines can be used with any suitable type of steering mechanism. Additionally, although the preferred steering mechanism was described above as having two steering rings, a single steering ring can be used to steer the transducer assembly only in a single plane.

As described above, the housing 22 of the transducer assembly 10 connects to a cable of a medical diagnostic ultrasonic imaging system. It is preferred that the transducer assembly 10 be easily disconnected from the cable to allow the transducer assembly 10 to be disposed and to allow the cable to be reused with another transducer assembly. In such a situation, it may be preferred to increase the distance between the user's hand and the reusable cable to ensure that the reusable cable is not contaminated. Accordingly, it is preferred that the housing 700 comprise an extension portion 710 to ensure that the portion of the housing that the user grips to manipulate the steering rings (i.e., the handle portion 720) is sufficiently far away from the reusable cable to ensure that the reusable cable will remain sterile (see FIG. 7). It is preferred that the length of the extension portion 710 be greater than about five inches. Even with this length, a sterile sheath may be needed to cover the connection to the reusable cable. Accordingly, it is especially preferred that the length of the extension portion 710 be about three feet to allow a user to operate the transducer assembly 10 without the use of a sterile sheath. Further, it is preferred that the extension portion 710 comprise a flexible material so that the extension portion 710 will hang from the handle portion 720, making the handle portion 720 easier to hold and balance.

Turning again to FIG. 7, in addition to the handle portion 720, the housing 700 (or controller 700) also comprises a control portion 730. In this preferred embodiment, the control portion 730 comprises a first steering actuator 732, a second steering actuator 734, and a braking actuator 736, which are each rotatable about a longitudinal axis A extending between the handle portion 720 and the control portion 730. Although the actuators 732, 734, 736 are in the form of rings in the embodiment shown in FIG. 7, it should be noted that the actuators 732, 734, 736 can take any desired form. As described above, rotation of the first steering actuator 732 about the longitudinal axis A steers the conduit in a first plane (e.g., in the anterior/posterior plane), and rotation of the second steering actuator 734 steers the conduit in a second plane (e.g., in the left/right plane). Further, rotation of the braking actuator 736 restricts rotation of at least one of the first and second steering actuators 732, 734.

Figure 7:
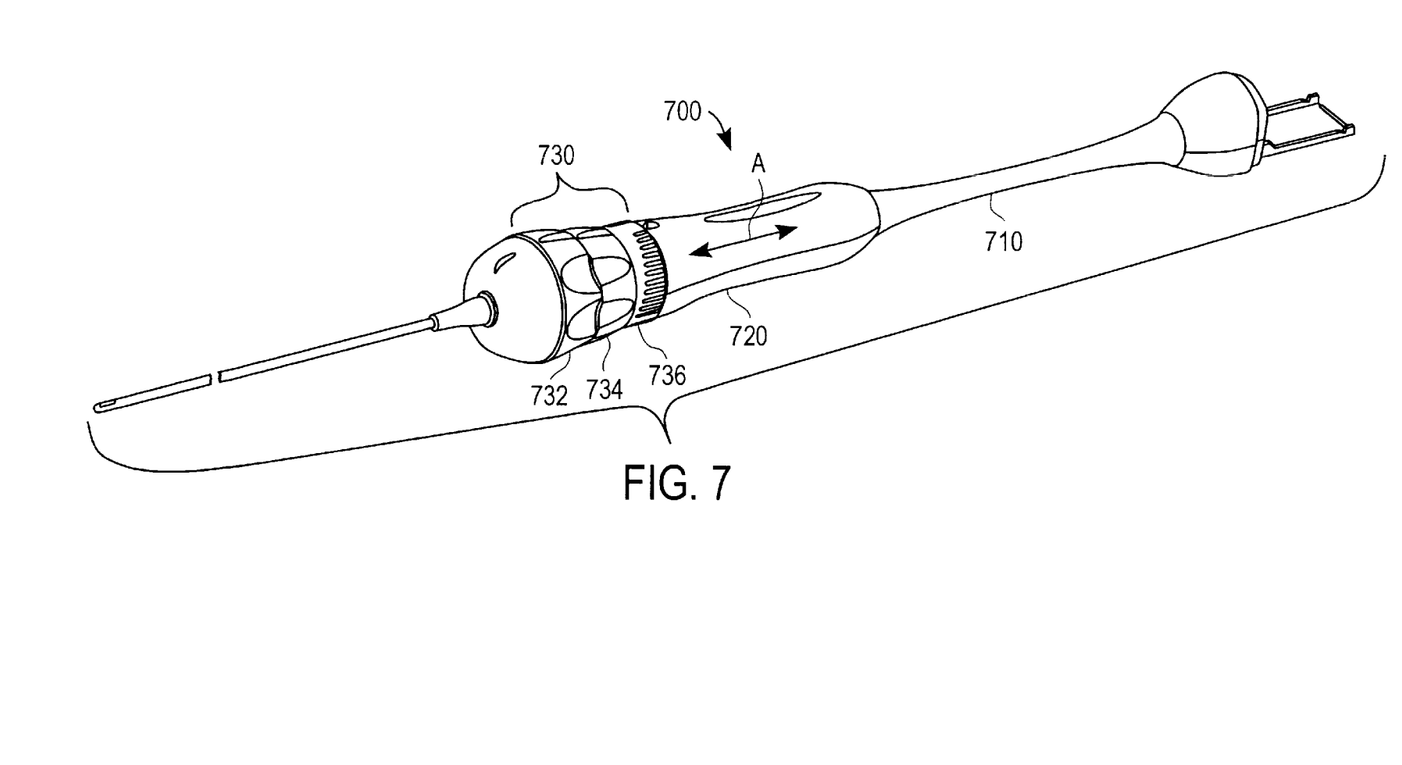
FIG. 7 is a perspective view of an ultrasonic transducer assembly controller of another presently preferred embodiment.
Figure 8:
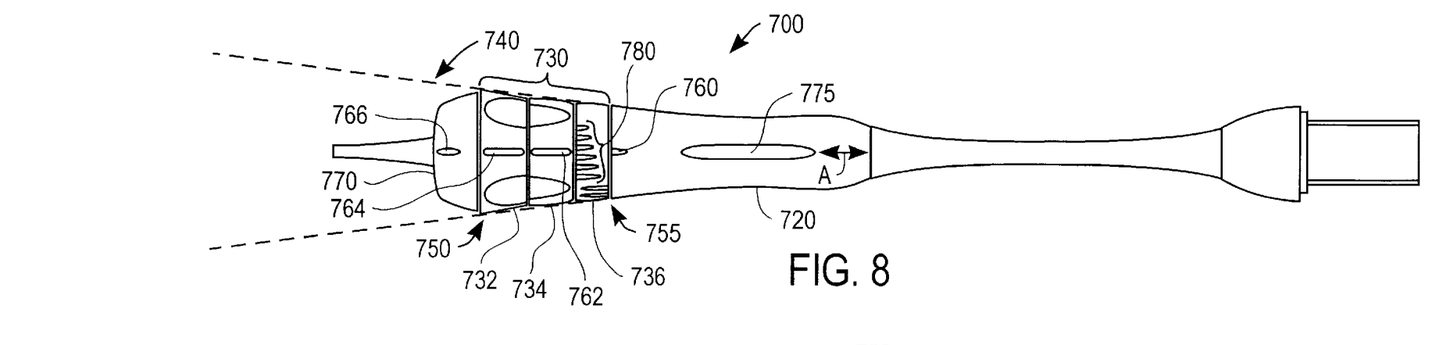
FIG. 8 is a top view thereof.

Turning now to FIG. 8, which is a top view of the controller 700 of FIG. 7, it can be seen that the control portion 730 has a partial-conical shape 740 such that the control portion 730 conically tapers from a relatively wider width at a distal end 750 of the control portion 730 to a relatively narrower width at a proximal end 755 of the control portion 730. More specifically, the first and second steering actuators 732, 734 are tapered such that the actuators 732, 734 have a smaller diameter at an end proximal to the handle portion 720 and a larger diameter at an end distal to the handle portion 720. This shape is compatible with the natural form that a human hand holds. Specifically, the first few fingers of an operator's hand want a larger turning radius, while the bottom fingers want a narrower holding diameter. Accordingly, this conical shape is more natural than a cylindrical shape. The diameters are preferably designed to provide a continuous conical form such that an operator's fingers can easily slide between the two steering actuators 732, 734 for efficient use. Although the two steering actuators 732, 734 form a continuous conical form, the steering actuators 732, 734 are still discernible diameters that allow an operator to distinguish the two steering actuators 732, 734 from one another.

Figure 13:
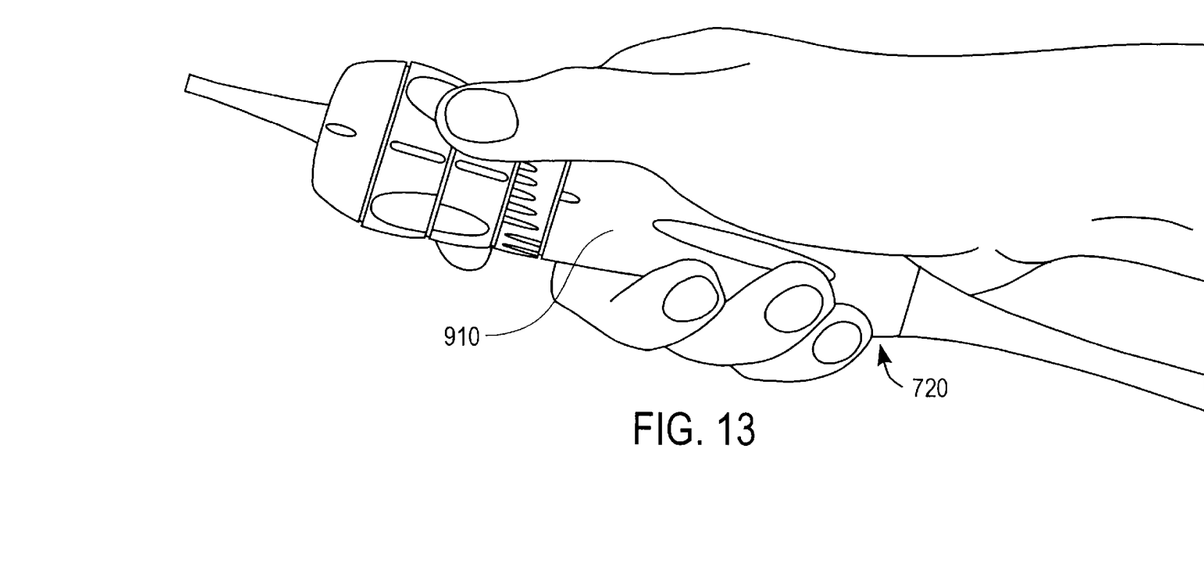
FIG. 13 is a perspective view illustrating a one-handed operation of actuators of the controller of FIG. 7.

The conically-sculptured controller form comfortably fits a variety of hand sizes and provides a variety of holding positions to allow the operator's fingers to conveniently rotate the actuators 732, 734, 736 with one hand, as shown in FIG. 13. Accordingly, this ergonomically-designed controller fits the conical space that the hand naturally grasps when holding an object and allows one-handed operation of the actuators 732, 734, 736. It should be noted that one steering actuator or more than two steering actuators can be used. Additionally, the controller can have multiple braking actuators, e.g., one braking actuator for each of the two steering actuators. Further, the controller can have a steering actuator without a braking actuator.

Figure 9:
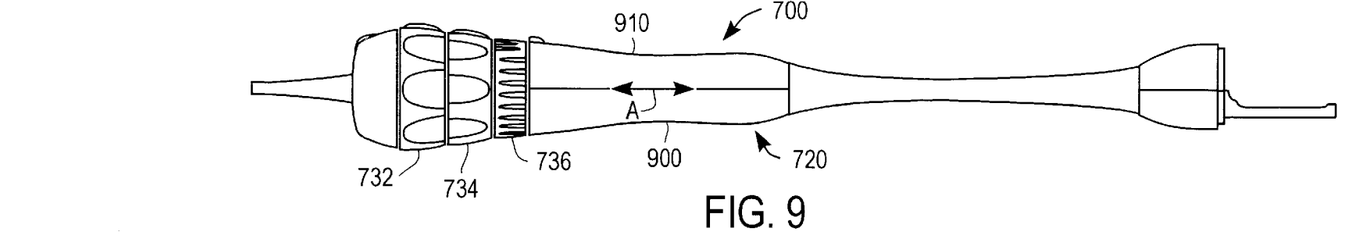
FIG. 9 is a side view thereof.

As shown in FIG. 9, which is a left-side view of the controller 700, each steering actuator 732, 734 defines a set of recesses to provide touch location indication by an operator's fingers to rotate the steering actuators 732, 734. In this preferred embodiment, the recesses are scalloped recesses designed to fit an operator's fingers. The recesses are within the steering actuators' 732, 734 outer surface on one side and extend past the steering actuators' 732, 734 outer surface on the other side. The two steering actuators 732, 734 have the open end of the recesses facing each other, providing tactile positioning when the operator feels the matched edges of the outer surfaces of adjacent steering actuators 732, 734.

Figure 11:
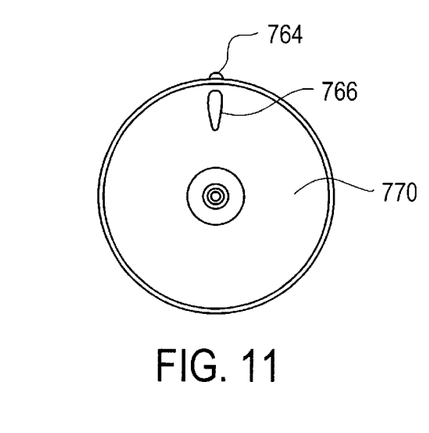
FIG. 11 is a front view thereof.
Figure 12:
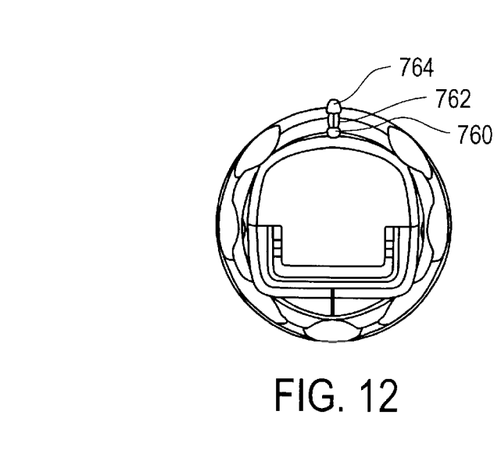
FIG. 12 is a rear view thereof.

As shown in FIG. 8, the controller 700 also comprises position indicators 760, 762, 764, 766 on the handle portion 720, the second steering actuator 734, the first steering actuator 732, and a nosecap 770 of the controller 700, respectively. The position indicators are also shown in FIGS. 11 and 12, which are front and rear views, respectively, of the controller 700. The position indicators 760, 762, 764, 766 provide an operator with tactile and visual reference of a neutral position. For example, when all the position indicators 760, 762, 764, 766 are aligned, the operator knows that the conduit is in a neutral position (i.e., there is no anterior/posterior or left/right bias on the conduit). Further, when only one position indicator of one steering actuator is aligned with the position indicators 760, 766 of the handle portion 720 and nosecap 770, the operator knows that the conduit is in a neutral position in one, but not both, planes. Displacement of a position indicator with respect to the neutral position also provides an indication of the degree of steering of the conduit. In this preferred embodiment, the position indicators 760, 762, 764, 766 take the form of raised ridges, although other forms, such as, but not limited to, recesses and/or graphical indicators, can be used. It is important to note that fewer or more position indicators than those shown in the drawings can be used.

Referring again to FIG. 8, the handle portion 720 defines an oval shape 775 providing visual and tactile alignment of the controller 700. The oval shape 775 is aligned with the position indicators 760, 766 of the handle portion 720 and the nosecap 770 to further orient the operator to the neutral-operation position. Of course, other, non-oval shapes can be used.

Figure 10:
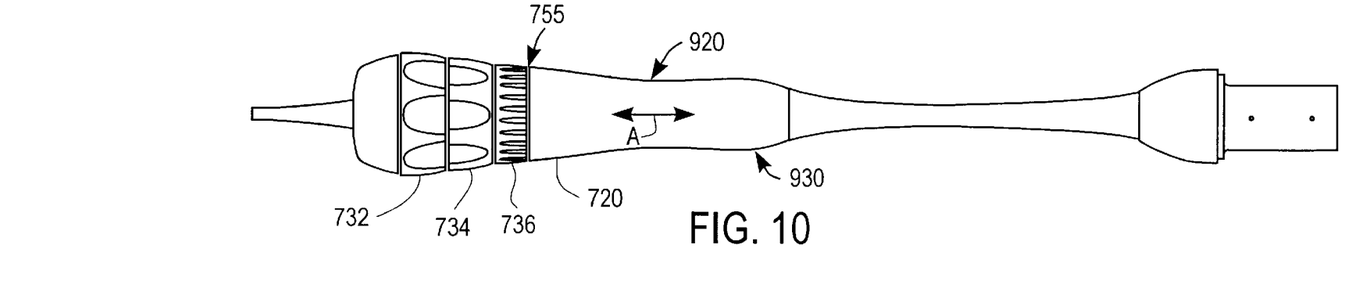
FIG. 10 is a bottom view thereof.

As shown in FIG. 10, which is a bottom view of the controller 700, the braking actuator 736 preferably has about the same diameter as the proximal end of the second steering actuator 734 so that the operator's fingers can easily move from the braking actuator 736 to the two steering actuators 732, 734. The braking actuator 736 provides grip through a set of small recessed scallops, which in this preferred embodiment are within the braking actuator's 736 outer surface on one side and extend past the braking actuator's 736 outer surface on the other side. The set of recessed scallops provide finger grip for rotational force around 80% of the diameter of the braking actuator 736. As shown in FIG. 8, the braking actuator 736 also has a tactile and visual brake-force indicator 780 located in the remaining 20% of the braking actuator 736. In this preferred embodiment, the brake-force indicator 780 takes the form of a set of raised ridges forming a ramped group, where the raised detail on one end is long (indicating high brake force) and the raised detail on the other end is short (indicating low brake force).

Turning again to FIG. 9, the handle portion 720 comprises a palm-resting portion 900 and a finger-resting portion 910 on substantially opposite sides of the handle portion 720. The palm-resting portion 900 has a slight thinning to allow the thicker portion of the back of the hand to fit and locate the handle portion 720. As shown in FIG. 13, the finger-resting portion 910 allows the last three fingers of the operator's hand to rest against the handle portion 720. The oval shape located on the finger-resting portion 910 provides a balanced grip through its tapered form.

As shown in FIG. 10, the controller 700 tapers from a relatively narrower width at the proximal end 755 of the control portion 730 to a relatively narrower width at a first location 920 in the handle portion 720. In this preferred embodiment, the first location 920 is between an end of the handle portion 720 that is distal to the control portion and an end that is proximal to the control portion. The handle portion then expands from the relatively narrower width at the first location 920 in the handle portion 720 to a relatively wider width at a second location 930, which is at the distal end of the handle portion 720. This provides a positive grip so the controller 700 does not slide out of the operator's hand. Of course, other shapes are possible. For example, the handle portion 720 can continue in the conical shape defined by the control portion 730, such that the controller 700 tapers from the width at the proximal end 755 of the control portion 730 to a relatively narrower width at the distal end of the handle portion 720. Further, the handle portion 720 can take a generally cylindrical shape, such that the handle portion 720 extends, with about the same width, from the first location to a second location closer to the distal end of the handle portion.

Figure 14:
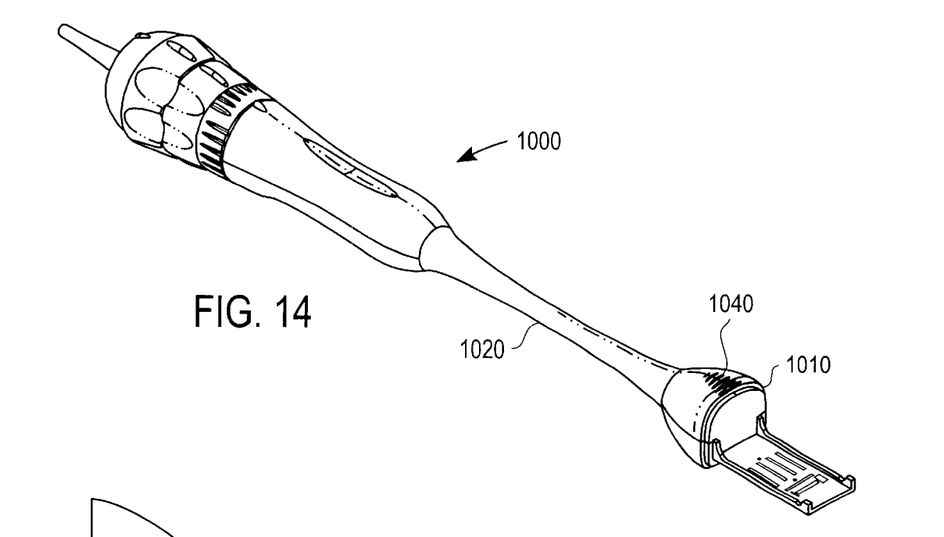
FIG. 14 is a perspective view of an ultrasonic transducer assembly controller of another presently preferred embodiment.
Figure 15:
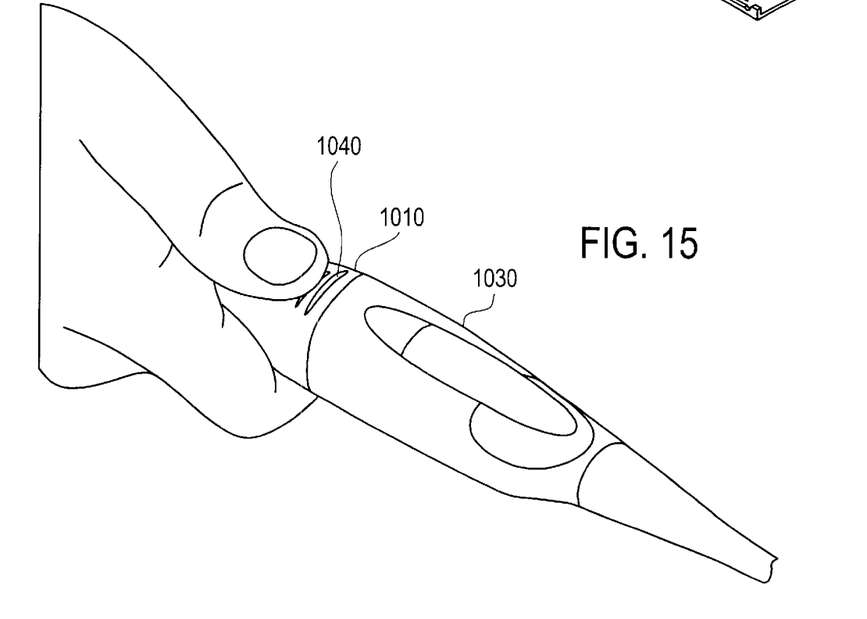
FIG. 15 is an illustration of the ultrasonic transducer assembly controller of FIG. 14 connected to a cable of a medical diagnostic ultrasonic imaging system.

Turning again to the drawings, FIG. 14 is a perspective view of an ultrasonic transducer assembly controller 1000 of another presently preferred embodiment. In this preferred embodiment, a connector portion 1010 is located at the terminating end of the extension portion 1020. The connector portion 1010 is shaped to connect the controller 1000 to a cable 1030 of a medical diagnostic ultrasonic imaging system, as shown in FIG. 15. In this preferred embodiment, the connector portion 1010 comprises a finger grip portion 1040 that allows an operator to easily couple and decouple the connector portion 1010 with the cable 1030. The finger grip portion 1040 also provides a tactile and visual reference for the separation line between the disposable catheter controller portion and the non-disposable connector portion, which is important to comply with sterile requirements.

It should be clearly understood that the foregoing detailed description has described only a few of the many forms that the present invention can take and that a wide range of changes and modifications can be made to the preferred embodiments described above. It is only the following claims, including all equivalents, that are intended to define the scope of this invention.

What is claimed is:

1. A steering mechanism for an ultrasonic transducer assembly of the type comprising: an elongated conduit comprising a distal end portion and a proximal end portion; a plurality of ultrasonic transducer elements carried by the conduit adjacent the distal end portion; and a set of steering lines comprising a first steering line carried by the conduit; said steering mechanism comprising:

a housing defining a longitudinal axis extending generally parallel to the proximal position of the conduit;

a steering actuator mounted for rotation about the longitudinal axis, said steering actuator accessible to a user around a complete circumference of the housing;

a steering hub carried by the steering actuator for rotation about the longitudinal axis, said steering hub being adapted to secure the first steering line thereto such that rotation of the steering hub alters the effective length of the first steering line to steer the distal end; and a stator carried by the housing adjacent the steering hub, said stator being adapted to have said first steering line wrap at least partially around an outer diameter of the stator before securing to the steering hub.

2. The invention of claim 1, wherein the stator comprises a set of bearings positioned around the outer diameter of the stator.

3. The invention of claim 1, wherein the stator comprises a set of pins positioned around the outer diameter of the stator.

4. The invention of claim 1, wherein the stator comprises a set of rollers positioned around the outer diameter of the stator.

5. The invention of claim 1, wherein the housing further comprises a shaft coupled with the conduit and extending along the longitudinal axis, said shaft adapted to route the first steering line from the longitudinal axis.

6. The invention of claim 5, wherein the shaft defines a slot adapted to route therethrough the first steering line from the longitudinal axis.

7. The invention of claim 6 further comprising a bearing adjacent to said slot.

8. The invention of claim 6 further comprising a pin adjacent to said slot.

9. The invention of claim 6 further comprising a roller adjacent to said slot.

10. The invention of claim 1, wherein the set of steering lines additionally comprises a second steering line, wherein said steering hub is adapted to secure the first and second steering lines thereto and wherein said stator is adapted to have said second steering line wrap at least partially around the outer diameter of the stator in an opposite direction from said first steering line before securing to the steering hub.

11. The invention of claim 1, wherein the set of steering lines additionally comprises a second steering line, and wherein the steering mechanism further comprises:

a second steering actuator mounted to the housing for rotation about the longitudinal axis, said second steering actuator accessible to a user around a complete circumference of the housing; and a second steering hub carried by the second steering actuator for rotation about the longitudinal axis and adapted to secure the second steering line thereto;

said stator adapted to have said second steering line wrap at least partially around the outer diameter of the stator before securing to the second steering hub.

12. The invention of claim 11, wherein the stator is positioned between the first and second steering hubs.

13. The invention of claim 11 further comprising a brake control element carried by the housing and coupled to the first and second steering actuators and to the stator such that rotation of the brake control element applies friction to the first and second steering actuators and to the stator to hold the steering actuators in a selected position with respect to the housing.

14. The invention of claim 1, wherein the steering line comprises a braided yarn spun from a liquid crystal polymer.

15. The invention of claim 14, wherein the braided yarn spun from a liquid crystal polymer comprises Vectran™.

16. The invention of claim 1, wherein the steering line comprises a monofilament extruded from a liquid crystal polymer.

17. The invention of claim 16, wherein the monofilament extruded from a liquid crystal polymer comprises Vectran™.

18. The invention of claim 1, wherein the housing is removablely couplable to a cable of an ultrasound imaging system, and wherein the housing further comprises a handle portion and a flexible extension portion.

19. The invention of claim 18, wherein the flexible extension portion is characterized by a length of greater than about five inches.

20. The invention of claim 18, wherein the flexible extension portion is characterized by a length of about three feet.

* * * * *